United States Patent [19]

Koh et al.

[11] Patent Number: 4,942,243
[45] Date of Patent: Jul. 17, 1990

[54] PROCESS FOR PREPARING N''-[4-[[(2-CYANOETHYL)THIO]METHYL]-2-THIAZOLYL]GUANIDINE

[75] Inventors: Moon G. Koh; Jai M. Shin; Dong S. Kim; Choon S. Lee, all of Seoul, Rep. of Korea

[73] Assignee: Hanil Pharmaceutical Ind., Co., Ltd., Seoul, Rep. of Korea

[21] Appl. No.: 179,267

[22] Filed: Apr. 8, 1988

[30] Foreign Application Priority Data

Mar. 11, 1988 [KR] Rep. of Korea .................. 2575-88

[51] Int. Cl.$^5$ .................................... C07D 277/48
[52] U.S. Cl. .................................................. 548/193
[58] Field of Search ........................ 548/193, 194, 197

[56] References Cited

U.S. PATENT DOCUMENTS 4,464,374 8/1984 Yellin ..................................... 548/193
4,762,932 8/1988 Yellin ..................................... 548/193

FOREIGN PATENT DOCUMENTS 0087274 2/1983 European Pat. Off. ............ 548/193
0128736 6/1984 European Pat. Off. ............ 548/193
3530061 8/1985 Fed. Rep. of Germany ...... 548/193
56-55383 5/1981 Japan .................................. 548/193

OTHER PUBLICATIONS

Starks, Phase Transfer Catalysis pp. 80–84 (1978).
Dehmlow, Phase Transfer Catalysis pp. 138–140 (1980).

*Primary Examiner*—Robert Gerstl
*Attorney, Agent, or Firm*—Birch, Stewart, Kolasch & Birch

[57] ABSTRACT

A process for preparing N''-[4-[[(2-cyanoethyl)thio]-methyl]-2-thiazolyl]guanidine which comprises reacting a dihaloacetone with an β-cyanoethylthiol in a two phase solvent system at a pH of 4.5–6.0 to produce a 1-halo-3-(2-cyanoethylthio)propanone and reacting the 1-halo-3-(2-cyanoethylthio) with an amidinothiourea.

6 Claims, No Drawings

PROCESS FOR PREPARING N"-[4-[[(2-CYANOETHYL)THIO]METHYL]-2-THIAZOLYL]GUANIDINE

BACKGROUND OF THE INVENTION (I) Field of the Invention

The present invention relates to a process for producing N"-[4-[[(2-cyanoethyl)thio]methyl]-2-thiazolyl]guanidine represented in the following formula (I) in high yield, which is a useful reaction intermediate for sulfamylamidine antisecretory agents:

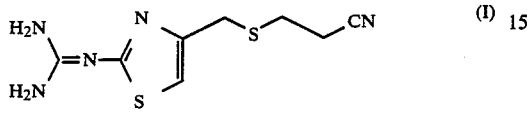

(II) Description of the Prior Art

Various processes for the preparation of N"-[4-[[(2-cyanoethyl)thio]methyl]-2-thiazolyl]guanidine are known in the art which are disclosed in European patent Nos. 87,274 and 128,736 published Aug. 31, 1983 and Dec. 19, 1984, respectively; unexamined Japanese Patent Application laid open under No. 56-55383 published May 15, 1981; German patent publication No. 3,530,061 published Aug. 22, 1985; and Journal of Organic Chemistry, vol. 26 (1961), 1443 by L. Bauer, et al. However, all of the prior art processes described above disclose various complicated steps and do not disclose an improved process for producing the N"-[4-[[(2-cyanoethyl) thio]methyl]-2-thiazolyl]guanidine in excellent yield in only one batch.

SUMMARY OF THE INVENTION

Accordingly, it is an object of the present invention to provide an improved process for the production of N"-[4-[[(2-cyanoethyl)thio]methyl]-2-thiazolyl]guanidine in high yield.

Another object of the present invention is to provide an improved process for preparing N"-[4-[[(2-cyanoethyl) thio]methyl]-2-thiazolyl]guanidine by utilizing a dihaloacetone and β-cyanoethylthiol as a starting material and a reactant, respectively.

Yet another object of the present invention is to provide an improved process for preparing N"-[4-[[(2-cyanoethyl) thio]methyl]-2 -thiazolyl]guanidine by utilizing an amidinothiourea as an additional reactant.

A further object of the present invention is to provide an improved process for preparing N"-[4-[[(2-cyanoethyl) thio]methyl]-2-thiazolyl]guanidine by utilizing only one batch at lower reaction temperatures.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to a process for preparing N"-[4-[[(2-cyanoethyl)thio]methyl]-2-thiazolyl]guanidine of formula (I) which comprises reacting a dihaloacetone of formula (II) with an β-cyanoethylthiol in a two phase solvent system at a pH of 4.5-6.0 to produce a 1-halo-3-(2-cyanoethylthio)propanone of formula (III), and reacting the 1-halo-3-(2-cyanoethylthio) of formula (III) with an amidinothiourea.

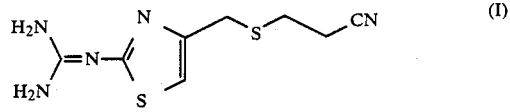

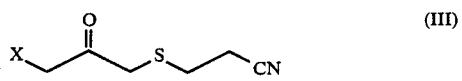

wherein X and Y are a halogen atom such as chlorine or bromine.

DESCRIPTION OF THE PREFERRED EMBODIMENTS

The present invention provides an economical process for the production of N"-[4-[[(2-cyanoethyl)thio]methyl]-2-thiazolyl]guanidine, in only one batch at a lower reaction temperatures, which is an important intermediate compound for preparing sulfamylamidine antisecretory agents such as a famotidine, 1-halo-3-(2-cyanoethylthio)propanone, or the like.

The present invention provides a process for preparing N"-[4-[[(2-cyanoethyl)thio]methyl]-2-thiazolyl]guanidine represented by the following formula (I):

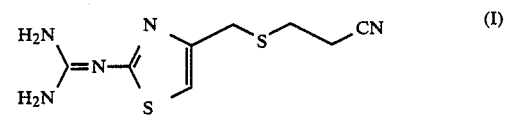

which comprises, (a) reacting a dihaloacetone of the following formula:

wherein X is a halogen atom such as chlorine or bromine atom; Y is a halogen atom such as a chlorine or bromine atom, with β-cyanoethylthiol in a two phase solvent system at pH 4.5-6.0 to obtain 1-halo-3-(2-cyanoethylthio)propanone of the following formula (III):

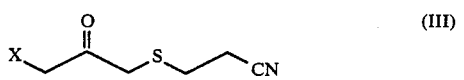

wherein X is as defined above; and (b) reacting the compound of formula (III) with an amidinothiourea.

The reaction scheme of the present invention is as follows:

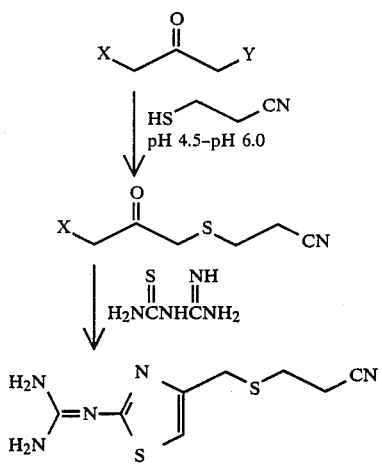

wherein X and Y are the same as defined above. The final product of formula (I) according to the present invention is produced in high yield. The reaction (a) is conducted at a temperature of 4° C. to 30° C., preferably at 20° C., in a two phase solvent system such as in chloroform-water, ethyl acetate-water, and ether-water, and preferably in a dichloromethane-buffer solution of pH 6.0. The reaction (a) is carried out at a pH of 4.5–6.0 by adding an aqueous basic solution such as, for example, 30% sodium phosphate tribasic solution, 25% sodium carbonate solution, saturated sodium bicarbonate solution, or 12% sodium hydroxide solution. It is very important to maintain a pH of 4.5–6.0 during the reaction. That is, the reaction (a) is very slowly carried out in acidic media (<pH 3.0) and the reaction gives some by-products in basic media (>pH 7.0). The β-cyanoethylthiol is prepared and purified by the process as previously described in L. Bauer and T. L. Welsh., J. Org. Chem., 1961, vol. 26, 1443. Also, the 2-cyanoethylthiol can be used without isolation of S-(β-cyanoethyl) isothiourea, or its hydrogen chloride salt is adjusted to a pH of 6.0 using phosphoric acid and used in situ for preparing the compound of formula (III) as described above.

The compound of formula (III), wherein X is as previously defined, is reacted with the amidinothiourea to produce the compound of formula (I) in high yield in a solvent such as lower alcohols, acetone, acetonitrile, and dimethylformamide. The reaction is carried out at a temperature of about 30° to 70° C., preferably, about 60° C., for a period of 3 hours to 10 hours.

The present invention will now be described in more detail in connection with the following examples which should be considered as being exemplary and not limiting the present invention.

EXAMPLE 1

1-chloro-3-(2-cyanoethylthio)propanone

A solution of 12.7 g of 1,3-dichloroacetone in 200 ml of dichloromethane is added to a solution of 8.7 g of β-cyanoethylthiol in aqueous buffer solution (pH 6.0: 100 ml), and is stirred at 20° C. at pH 4.5–6.0 by adding a solution of sodium phosphate, tribasic (30%). After stirring for 5 hours, the organic layer is separated, is dried over anhydrous sodium sulfate, and is concentrated to give pale yellow oil, which is purified in vacuo to give 16.3 g of 1-chloro-3-(2-cyanoethylthio)propanone.

IR(KBr): 2240(—CN), 1700(—CO) cm$^{-1}$
1H NMR(CDCl$_3$): δ4.4(2H, s), 3.6(2H, s), 2.8(4H, m).

The title compound is prepared similarly by reacting 1-bromo-3-chloroacetone with 2-cyanoethylthiol. When 1,3-dibromoacetone is employed in the procedure as described above in place of 1,3-dichloroacetone, 1-bromo-3-(2-cyanoethylthio)propanone is obtained in 94% yield.

EXAMPLE 2

N″-[4-[[(2-cyanoethyl)thio]methyl]-2-thiazolyl]guanidine

To a solution of 8.9 g of 1-chloro-3-(2-cyanoethylthio)propanone in 100 ml of acetone is added 6.3 g of amidinothiourea and the reaction mixture is stirred at 50° C. for 9 hours. Also, the reaction mixture is concentrated under reduced pressure, made basic with saturated sodium carbonate solution, and extracted with chloroformmethanol (10:1) solution (170 ml×2). The combined organic layer is dried over anhydrous magnesium sulfate, and is concentrated in vacuo to give a solid, which is crystallized from acetone-hexane to afford 10.2 g of the title compound, m.p.: 125°–128° C.

IR(KBr): 2240, 1640, 1590 cm$^{-1}$
1H NMR(CDCl$_3$-DMSO-d$_6$): δ6.9(4H, br), 6.5(1H, s), 3.8(2H, s), 2.7(4H, m).

The title compound is prepared similarly by reacting 1-bromo-3-(2-cyanoethylthio)propanone with amidinothiourea (82% yield).

There is illustrated an additional embodiment of a process for preparing N″-[4-[[(2-cyanoethyl)thio]methyl]-2-thiazolyl]guanidine in accordance with the present invention. 12.3 g of S-(β-cyanoethyl)isothiuronium chloride is stirred with ice-cooled 12% sodium hydroxide solution (50 ml) for 1 hour, and the reaction mixture is adjusted to a pH of 6.0 using 20% phosphoric acid solution. To the solution of β-cyanoethylthiol prepared as described above is added a solution of 6.3 g of dichloroacetone in 150 ml of ethylacetate, and this mixture is stirred for 5 hours at 20° C. while keeping the pH at 5.5. The ethyl acetate layer is separated, dried over anhydrous magnesium sulfate, and concentrated to give a pale yellow oil which is dissolved in 50 ml of acetonitrile. To a solution of acetonitrile prepared as described above is added a solution of 6.4 g of amidinothiourea in 100 ml of acetone, and this mixture is stirred at 60° C. for 8 hours. The reaction mixture is concentrated, made basic, and extracted with chloroformmethanol (10:1) solution. The organic layer is dried over anhydrous magnesium sulfate, and concentrated in vacuo. The residue is crystallized from acetone-hexane to give 9.2 g of the title compound (9.2 g).

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:
1. A process for preparing N″-[4-[[(2-cyanoethyl)thio]methyl]-2-thiazolyl]guanidine of the formula (I) in high yield which comprises the steps of:
   (a) reacting a dihaloacetone of formula (II) with a β-cyanoethylthiol to produce a 1-halo-3-(2-cyanoethylthio)propanone of the formula (III) in a two phase solvent system at a pH of about 4.5–6 at a temperature of about 4° to 30° C., and (b) reacting said 1-halo-3-(2-cyanoethylthio)propanone of formula (III) with an amidinothiourea at a temperature of about 30°–70° C. for about 3 to 10 hours so as to produced the guanidine of formula (I), wherein the formulas (I), (II), and (III) are as follows:

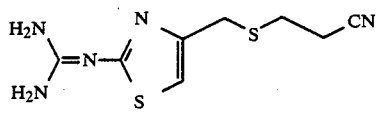
(I)

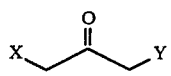
(II)

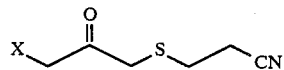
(III)

wherein X and Y are a halogen atom such as chlorine or bromine.

2. The process of claim 1, wherein the reaction step (a) is conducted at a temperature of about 20° C.

3. The process of claim 1, wherein the reaction step (a) is conducted at a pH of about 6.0.

4. The process of claim 1, wherein the two phase solvent system comprises a combination of two solvents selected from the group consisting of chloroform and water, ethylacetate and water, ether and water, and dichloromethane and a buffer solution.

5. The process of claim 4, wherein the two phase solvent system is dichloromethane and a buffer solution.

6. The process of claim 1, wherein the reaction step (b) is conducted at a temperature of about 60° C.

* * * * *